(12) United States Patent
Beauchamp

(10) Patent No.: US 7,160,479 B2
(45) Date of Patent: Jan. 9, 2007

(54) METHOD AND APPARATUS FOR EVALUATING PANEL DRIP TESTS

(75) Inventor: Phillip J. Beauchamp, Warren, MI (US)

(73) Assignee: PPG Industries Ohio, Inc., Cleveland, OH (US)

( * ) Notice: Subject to any disclaimer, the term of this patent is extended or adjusted under 35 U.S.C. 154(b) by 343 days.

(21) Appl. No.: 10/761,080

(22) Filed: Jan. 20, 2004

(65) Prior Publication Data

US 2005/0170097 A1 Aug. 4, 2005

(51) Int. Cl.
*C03C 15/00* (2006.01)

(52) U.S. Cl. ............................. 216/84; 216/85; 216/92; 216/97

(58) Field of Classification Search .................. 216/84, 216/85, 92, 97
See application file for complete search history.

(56) References Cited

U.S. PATENT DOCUMENTS 5,567,981 A 10/1996 Bhansali et al.
5,756,885 A * 5/1998 Poku et al. .................... 73/104
2003/0034550 A1 2/2003 Nakatani
2004/0179193 A1* 9/2004 Maezono et al. ........ 356/239.1

OTHER PUBLICATIONS

GM Engineering Standards Material Specification Pating #9984304, p. 3, section 3.3.4.4, Jun. 2001.

* cited by examiner

*Primary Examiner*—Nadine Norton
*Assistant Examiner*—Binh X Tran
(74) *Attorney, Agent, or Firm*—Carol A. Marmo; Deborah M. Altman

(57) ABSTRACT

The apparatus for quantifying effectiveness of solvent to clean a coating from a substrate using a drip test includes a test stand, a drip test device, and a computer associated with the stand and test device. The test stand is adapted to support a glass panel at a predetermined angle. The drip test device is adapted to deposit solvent-based droplets onto a coated surface of the glass panel to clean the coated surface. The computer optically scans the glass panel and to determine cleanliness after a drip test is conducted. The method includes conducting a drip test on a coated glass panel, placing a template behind the glass panel, optically scanning the glass panel and template into a computer, and evaluating the glass panel for cleanliness based on the scanned image of the glass panel and template.

15 Claims, 3 Drawing Sheets

METHOD AND APPARATUS FOR EVALUATING PANEL DRIP TESTS

BACKGROUND OF THE INVENTION

1. Field of the Invention

The present invention relates generally to panel drip testing used to evaluate the effectiveness of coating cleaners in removing coating from a coated surface and, more particularly, to a method and apparatus for quantitatively evaluating the results of panel drip tests.

2. Description of Related Art

Blends of solvents are typically used to clean-up coating residues in many coating applications. One such use of these solvent blends is the purging or cleaning of coating residue in automated coating application equipment between color changes. The performance of these solvent blends is crucial to ensure proper coating application and maintenance of the equipment.

Laboratory testing methods have been used in the purge solvent industry to compare one blend of solvents to another. The most common test to screen or evaluate solvent blends is collectively known in the industry as the "drip" test. In this test, a specified film thickness of coating (i.e., coating) is applied to a clean glass test plate. The coated glass test plate is allowed to air dry for a specified number of minutes and then placed in a rack at a fixed angle. The solvent blend to be tested is then dripped onto the film at a fixed rate and the coated glass test plate is removed after a predefined number of drips have hit the surface of the glass test plate. Alternatively, the drip test may be discontinued after a set or defined portion of the glass test plate has been cleaned by the solvent blend. The glass test plate is then compared to a control solvent applied using the same parameters. A typical setup for such drip tests would involve a glass test plate coated with 1.5 mil of coating dried for 2 minutes, and then applying a solvent at a rate of 1 drop per second until 10 drops have been applied.

The solvent dissolves away a portion of the coating from the coated surface. When evaluating several solvent blends to determine the optimum product, the glass test plates treated with the different solvent blends are compared visually and the rough area where the solvent cleaned the glass test plate is compared. Many solvent blends are easily visually differentiated through this test, allowing the experimenter to quickly discern the better purge solvent product. Some solvent blends, however, are not so easily visually differentiated and there are no quantitative measures currently available in the art to differentiate between various solvent blends. Thus, the relative effectiveness of solvent blends tested using a drip test is often dependent on the experimenter's subjective interpretation.

Methods and devices are known in the art for evaluating the surface quality such as roughness or scratches and other parameters of materials and substrates using ultrasound, lasers, and the like.

Methods and devices are specifically known in the art for detecting faults in and evaluating the quality of flat glass panels using, for example, infrared sensors, and/or video cameras to monitor an illuminating device passing below the glass. The change of intensity of the two video signals is then used to evaluate the optical quality of the glass panel and locate faults within the glass panel.

Even though such methods and devices are known in the art for detecting and evaluating the surface quality and other parameters of materials and substrates, these methods and devices are not generally applicable to evaluating panel drip tests. In view of the foregoing, a need exists in the field of panel drip tests for a method of objectively evaluating the results of panel drip tests. More particularly, a need exists in the field of panel drip tests for a method of quantitatively evaluating panel drip tests, for example by use of a mathematical algorithm. Additionally, a need exists for a method of quantitatively rating glass panels tested using drip tests to provide quantitative results that would allow the best solvent to be selected from a number of tested glass panels. Further, a need exists for an improved apparatus by which panel drip tests are conducted, recorded, and evaluated. A method and apparatus for evaluating glass quantitatively the ability of a solvent to clean a coating from a substrate using a panel drip test provided in accordance with the present invention fulfills the foregoing needs.

SUMMARY OF THE INVENTION

The method of the present invention generally includes several steps, including conducting a drip test on a coated glass panel, placing a template behind the glass panel, digitally acquiring an image of the glass panel and template into a computer, and evaluating the glass panel for cleanliness based on the digital image of the glass panel and template.

The template may have a contrasting color or pattern thereon, such as a checkerboard pattern, a contrasting solid color, gray scales, or a custom-designed pattern, and the like. The method may further comprise processing the digitized image of the glass panel and template to determine the actual area of the glass panel cleaned by the drip test greater than a pre-specified value. The pre-specified value may be a pre-specified percentage.

The apparatus of the present invention for evaluating quantitatively the ability of a solvent to clean a coating from a substrate using a glass panel drip tests is generally comprised of a test stand, a drip test device, preferably a digital imaging device such as a digital camera or scanner, and a computer associated with the test stand and drip test device. The test stand is generally adapted to support a glass panel at a predetermined angle. The drip test device is generally adapted to deposit a preset number of solvent-based droplets onto a coated surface of the glass panel to clean the coated surface of coating. The computer is generally adapted to digitally acquire an image of the glass panel and determine cleanliness of the glass panel surface after a drip test is conducted using the drip test device.

The apparatus may further include a template positioned behind the glass panel. The template may have a contrasting color or pattern thereon. The template color or pattern may be a checkerboard pattern, a contrasting solid color, gray scales, or a custom-designed pattern, and the like. The computer may be programmed to process the digital image of the glass panel and template to determine the actual area of the glass panel cleaned by the drip test greater than a pre-specified value. The pre-specified value may be a pre-specified percentage. The test stand of the apparatus may include opposing sidewalls defining slots therein adapted to support the glass panel at the preset angle.

In another embodiment, the method of evaluating quantitatively the ability of a solvent to clean a coating from a substrate using a glass panel drip test generally includes several steps, including conducting a drip test on a coated glass panel, placing a template behind the glass panel, optically scanning the glass panel and template into a computer to form a digital image of the glass panel surface, and processing the digital image of the glass panel surface to determine cleanliness of the area of the glass panel surface subjected to the drip test. The template may have a contrasting color or pattern thereon, such as a checkerboard pattern, a contrasting solid color, gray scales, or a custom-designed pattern, and the like.

The method step of processing the digital image may comprise determining the actual area of the glass panel surface subjected to the drip test greater than a pre-specified value. The pre-specified value may be a pre-specified percentage.

Additionally, the method may further comprise evaluating the pixels of the digital image using a computer algorithm to determine how many pixels from the area of the glass panel surface subjected to the drip test have been cleaned. The step of evaluating the pixels may comprise identifying a reference clean pixel from an uncoated area of the glass panel surface, identifying a reference dirty pixel from a coated area of the glass panel surface not subjected to the drip test, and comparing individually the pixels from the area of the glass panel surface subjected to the drip test with the reference clean and dirty pixels. The step of comparing individually the pixels from the area of the glass panel surface subjected to the drip test with the reference clean and dirty pixels may further comprise calculating percent of cleanliness of each of the pixels from the area of the glass panel subjected to the drip test relative to the reference clean and dirty pixels. The cleanliness values of each of the pixels from the area of the glass panel subjected to the drip test may be displayed as a graph, such as a histogram on, for example, a computer screen of the computer for evaluation purposes. Additionally, the step of evaluating the pixels may comprise using image analysis of the pixels to quantify the actual area of the glass panel cleaned by solvent used in the drip test greater than a pre-specified value (i.e., a percentage).

Moreover, the method may further comprise assigning color values to the pixels of the digital image and evaluating the color values using the computer algorithm to determine how many pixels from the area of the glass panel surface subjected to the drip test have been cleaned. The step of evaluating the color values may comprise identifying the color value of a reference clean pixel from an uncoated area of the glass panel surface, identifying the color value of a reference dirty pixel from a coated area of the glass panel surface not subjected to the drip test, and comparing individually the color values of the pixels from the area of the glass panel surface subjected to the drip test with the color values of the reference clean and dirty pixels. The step of comparing individually the color values of the pixels from the area of the glass panel surface subjected to the drip test with the color values of the reference clean and dirty pixels may further comprise calculating percent of cleanliness using the color values of the pixels from the area of the glass panel subjected to the drip test relative to the color values of the reference clean and dirty pixels. The cleanliness values of each of the pixels from the area of the glass panel subjected to the drip test may be displayed as a graph, such as a histogram on, for example, a computer screen of the computer for evaluation purposes.

Further details and advantages of the present invention will become apparent when reading the following detailed description in conjunction with the accompanying drawings.

DETAILED DESCRIPTION OF THE INVENTION

Figure 1:
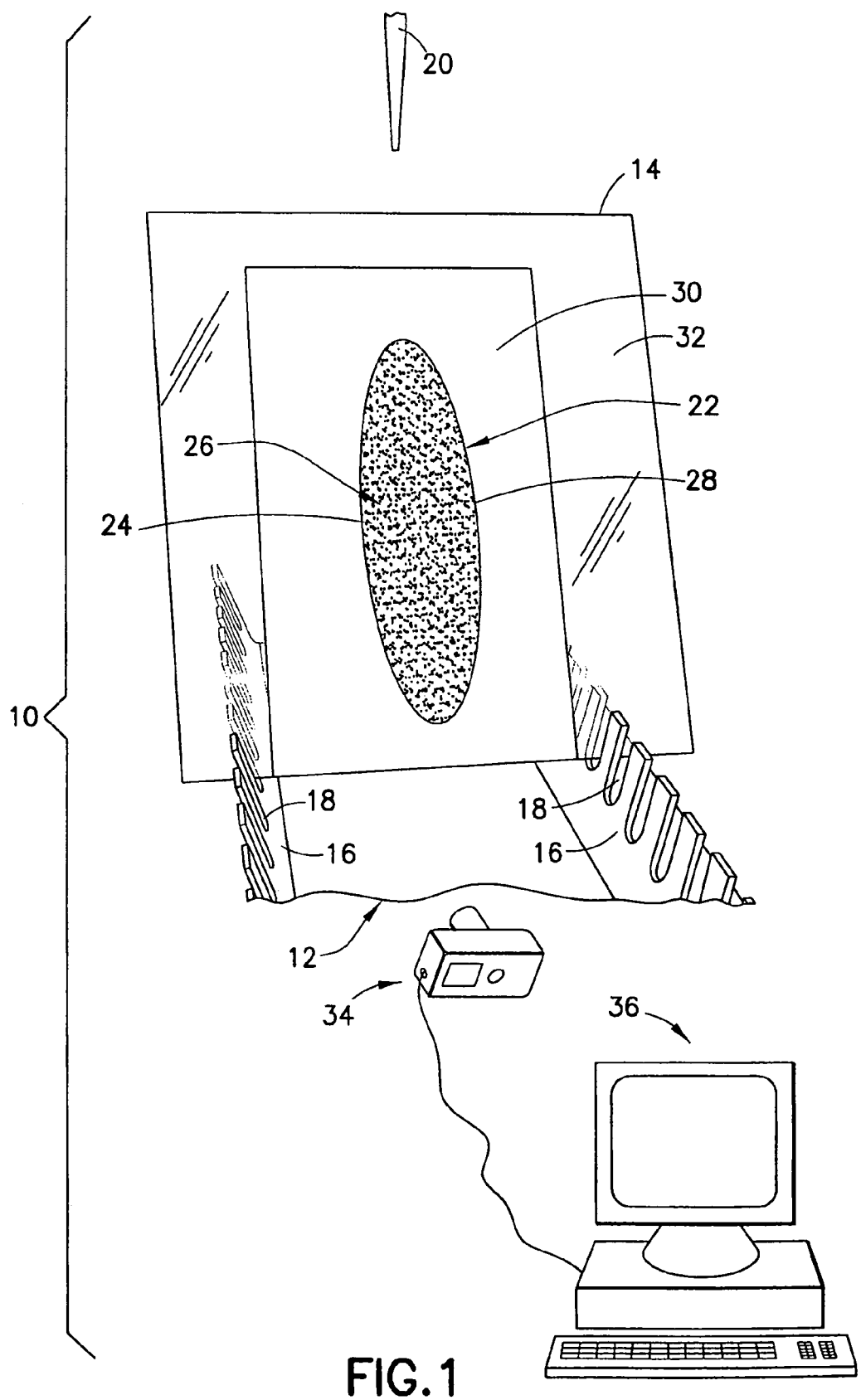
FIG. 1 is a perspective view of an apparatus for conducting, evaluating, and recording panel drip tests in accordance with the present invention.

For purposes of the description hereinafter, the terms "upper", "lower", "right", "left", "vertical", "horizontal", "top", "bottom", and derivatives thereof shall relate to the invention, as it is oriented in the drawing figures. However, it is to be understood that the invention may assume many alternative variations and step sequences except where expressly specified to the contrary. It is also to be understood that the specific devices and processes illustrated in the attached drawings and described in the following text are simply exemplary embodiments of the invention. Hence, specific dimensions and other physical characteristics related to the embodiments disclosed hereinafter are not to be considered limiting.

Figure 2:
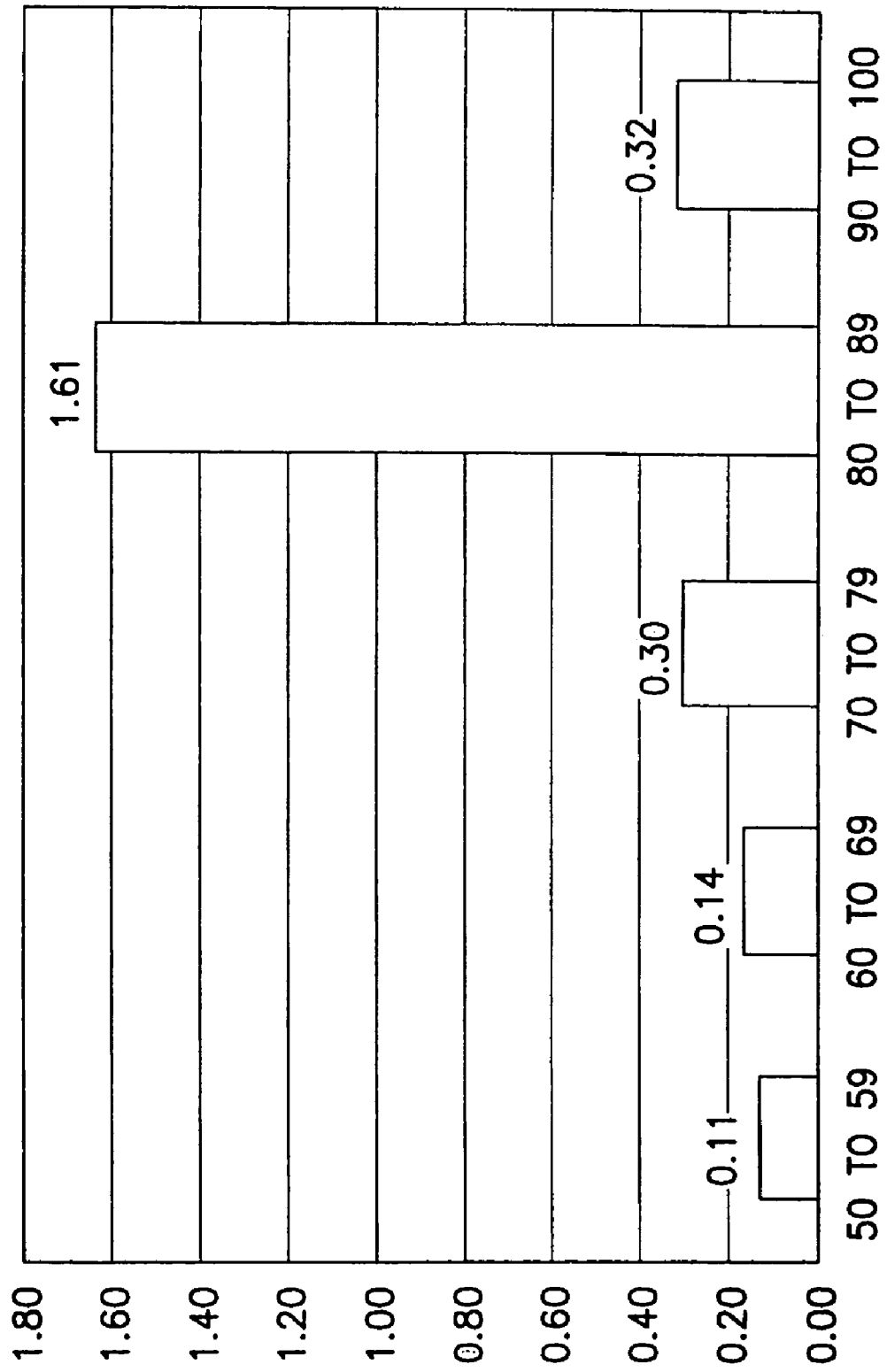
FIG. 2 is a representative graphical display for evaluating panel drip tests in accordance with the present invention.

Referring to FIGS. 1 and 2, an apparatus 10 for conducting glass panel drip tests and for quantitatively evaluating the ability of a solvent to clean a coating from a substrate using a glass panel drip test in accordance with the present invention is generally shown. The apparatus 10 includes a test stand 12 adapted to support one or more panels, preferably glass panels 14, as depicted in FIG. 1. The test stand 12 includes opposing sidewalls 16 defining opposing slots 18 for supporting the glass panel 14. The opposing slots 18 are formed at an angle relative to vertical for supporting the glass panel 14 at a predetermined or pre-selected angle, such as 45° or 60°. The glass panel 14 is coated or coated with a layer or film of coating that is to be subjected to a solvent drip test.

The apparatus 10 further includes a drip test device 20 positioned generally above the coated glass panel 14 to be tested in the apparatus. The drip test device 20 is adapted to apply a steady drip of solvent-based cleaning liquid onto the coated glass panel 14 and, more particularly, onto a targeted area 22 on the coated glass panel 14. The drip test may be discontinued after a predefined portion of the coated glass panel 14 has been cleaned. Alternatively, the drip test device 20 could be adapted to drip a set number of droplets onto the targeted area 22 of the coated glass panel 14 and the results compared with other cleaners at the same usage level, as is known in the art and explained previously. As indicated previously, panel drip tests are conducted to determine the number of drips or droplets of a solvent (or solvent blend) that must be applied to a coated substrate to "clean" an area on the coated substrate. This is a measure of the ability of a solvent (or solvent blend) to effectively clean a coating from a substrate. Accordingly, the drips or droplets of solvent applied by the drip test device 20 to the targeted area 12 on the coated glass panel remove in whole or in part the existing coating layer from the targeted area 22. The apparatus 10 and methods generally described herein this disclosure provide means by which the ability of a solvent (or a solvent blend) to remove a coating from a substrate can be determined quantitatively and objectively using a glass panel drip test.

In one embodiment of the method in accordance with the present invention, a template 24 is placed behind the inclined glass panel 14 prior to or after conducting the panel drip test. The template 24 is typically provided with a contrasting color or pattern 26 thereon to enhance visual or digital analysis of the glass panel 14 to be tested by the panel drip test. In particular, a contrasting pattern is provided to improve visual analysis of panel drip tests, while a contrasting color is usually provided to improve digital analysis of panel trip tests. The contrasting color is selected to contrast with the color of the coating on the glass panel 14 as explained further herein. The panel drip test is then generally conducted as follows.

Initially, the drip test device 20 applies a steady drip of cleaning solvent onto the coated glass panel 14 and, particularly, onto the targeted area 22 on the coated glass panel 14. The cleaning liquid forms a "cleaned" area 28 on the glass panel 14. The cleaned area 28 is typically surrounded by an "uncleaned" or still-coated area 30. The coated area 30 is in turn surrounded by a border area of uncoated glass 32.

Once the drip test has been conducted, a digital camera 34 or similar digital optical recording device, such as a digital scanner, is used to obtain a digital image of the glass panel 14 and template 24, typically located behind the "cleaned" area 28 on the glass panel 14. The digital image of the glass panel 14 and template 24 is provided to a computer 36, which can be operatively connected to the digital camera or scanner 34 for processing of the digital image and, typically, quantitative evaluation of the digital image. The contrasting color/pattern 26 on the template 24 provides a contrasting background to enhance evaluation of the of the glass panel 14. As indicated previously, a contrasting pattern is provided on the template 24 if the glass panel 14 is to be evaluated visually only, and a contrasting color is provided on the template 24 if the glass panel is to be evaluated digitally through use of a computer, as discussed herein. The contrasting color for the contrasting color/pattern 26 enhances the ability of the computer 36 to differentiate between "clean" and "dirty" areas on the targeted area 22 on the glass panel 14. If a contrasting pattern is used for the contrasting color/pattern 26 on the template 24, the contrasting pattern may be a checkerboard pattern, gray scales, or a custom-designed pattern, if the glass panel 14 is to be evaluated visually only. The checkerboard pattern for the contrasting color/pattern 26 is particularly suitable for visual evaluation of the panel drip tests in accordance with the present invention. If a contrasting color is used for the contrasting color/pattern 26, the contrasting color on the template 24 usually is a color that contrasts distinctly with the coating on the glass panel 14. For example, if the coating on the glass panel 14 is a shade of white, the contrasting color 26 on the template 24 typically a dark color such as a shade of black, dark gray, or dark brown, as shown in FIG. 1, and vice versa. The contrasting color for the contrasting color/pattern 26 is particularly suited for the digital analysis of the digital image in the computer 36, as discussed herein.

The computer 36 can be adapted to store and display the digital image of the glass panel 14 and template 24 for further processing, evaluation, and/or inspection. The computer 36 may be adapted to calculate actual area in square inches ($in^2$) or square centimeters ($cm^2$) of the cleaned area 28 in the targeted area 22 greater than a pre-selected value by analyzing the digital image of the glass panel 14 and template 24 pixel-by-pixel. For example, the computer 36 may be programmed to calculate the actual area (i.e., $cm^2$, $in^2$) in the cleaned area 28 greater than a pre-selected percentage value cleaned, such as 90% cleaned. The computer 36 may be further programmed to evaluate the cleaned area 28 to determine the actual area cleaned in the cleaned area 28 at different reference increments, such as 80% "clean", 70% "clean" and so on. The computer 36 may be further adapted to display the actual area cleaned at different cleanliness levels (i.e., 90% clean, 80% clean, and so on) as a graph, such as a histogram, for evaluation purposes, as shown in FIG. 2.

More particularly, the method of the present invention can apply image analysis to the digital image to quantify the cleanliness of the cleaned area 28 in the targeted area 22. The image analysis typically uses a computer mathematical algorithm to quantify the cleanliness of the cleaned area 28 in the targeted area 22 of the glass panel 14 resulting from the drip test. A well-known technique used in optical analysis is known in the art as Model RGB.

Model RGB is generally based on the fact that almost all the colors of the visible light spectrum may be displayed by mixing, in fixed proportions, three selected clusters of light of the properly chosen spectrum width. The three of components of Model RGB include red, green, and blue light (i.e., R=red, G=green, B=blue). A single component is the number proportional for intensity of a cluster of waves corresponding with the given cluster. Simultaneously emitting the three clusters representing components in proper proportions of energy can cause an impression in the human eye corresponding almost to white light. However, simultaneously emitting such three clusters in differently selected proportions can evoke the emerging of impressions of other colors in the eye. Model RGB is usually represented as a fragment of three-dimensional (3D) space, such as by use of a Cartesian coordinate system as generally illustrated in FIG. 3, discussed herein.

Referring now to FIGS. 1–5, the present invention utilizes Model RGB as part of a computer mathematical algorithm to evaluate the cleaned area 28 in the targeted area 22 on the glass panel 14. The cleaned area 28 may be designated as the total square inches ($in^2$) or total square centimeters ($cm^2$) cleaned, and is the area to be evaluated by the algorithm. More particularly, the cleaned area 28 may be designated as the total square inches ($in^2$) or total square centimeters ($cm^2$) cleaned above a certain percentage. As indicated, the typical method of obtaining the digital image or representation of the cleaned glass panel 14 is through the use of a digital scanner 34, as shown in FIG. 1.

The digital image or representation of the glass panel 14 and template 24 (with contrasting color thereon) captured by the digital scanner 34 is then processed in a pixel-by-pixel manner in the computer 36 to determine the RGB color of the target or test pixels. Using the computer algorithm provided on the computer 36, the target or test pixels of the cleaned area 28 are compared against two reference pixels. The two reference pixels include a reference "clean" pixel 40 from the uncoated glass 32 area, and a reference "dirty" pixel 42 from the coated or "uncleaned" area 30 on the glass panel 14. In particular, the color of the target or test pixels from the cleaned area 28 are compared to the color of the reference clean pixel 40, which represents clean glass, and the color of the reference dirty pixel 42, which represents uncleaned or unmodified coating film. The target or test pixels are sorted and counted according to how close they are in color compared to the clean glass color. The subtotals of the counted pixels may then be used with the DPI (Dots, or Pixels, per Inch) resolution of the digital image and the physical size of the glass panel 14 to produce a histogram of total area cleaned (in², cm²) in the cleaned area 28 relative to a pre-selected value, most often a pre-set percentage value.

Figure 3:
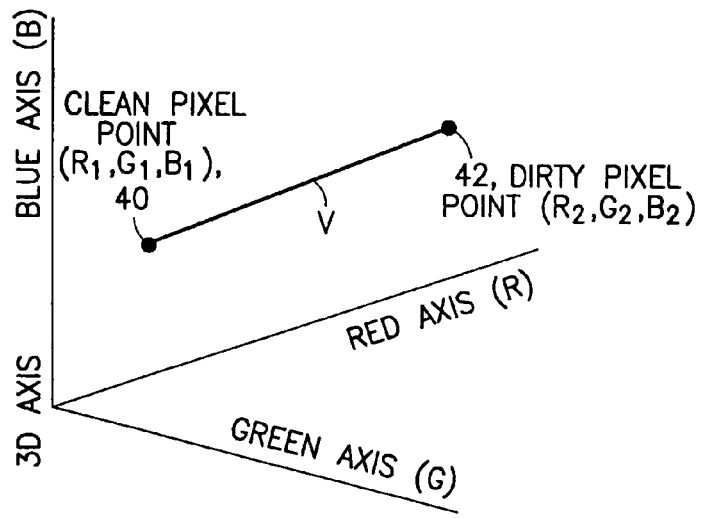
FIG. 3 is a Cartesian coordinate graphical representation of a mathematical algorithm used to evaluate panel drip tests in accordance with the present invention.
Figure 4:
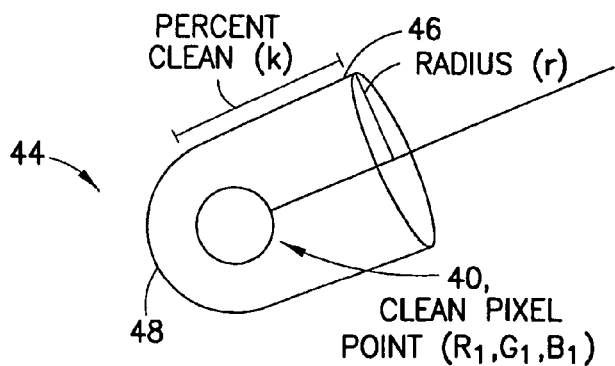
FIG. 4 is a three-dimensional (3D) representation of a portion of the graphical representation of the algorithm illustrated in FIG. 3.

Referring, in particular, to FIGS. 3 and 4, the reference clean and dirty pixels 40, 42 are shown. In the algorithm used in the method of the present invention, RGB point (0,0,0) corresponds to the color black while point (255,255, 255) corresponds to the color white. All colors present on the surface of the coated glass panel 14 may be represented by an RGB point (R,G,B) in the Cartesian coordinate system depicted in FIG. 3. A mathematical vector V is used in the algorithm to connect the reference clean and dirty pixels 40, 42. The RGB points between white and black generally represent the increase of color from white to black, as will be appreciated by those skilled in the art.

The mathematical vector V represents all the colors that should be encountered as the coating on the glass panel 14 is thinned and cleaned in the drip test. The cleaned area 28 where the coating has been dissolved may be processed pixel-by-pixel, as indicated previously, to identify the individual pixel's location in three-dimensional (3D) space relative to the vector V. The distance of the target or test pixel to the reference clean pixel 40 may be represented as a percentage of the total length of the vector V, which therefore provides an objective measurement of cleanliness of the target or test pixel.

In practice, not all of the individual target or test pixels from the cleaned area 28 will be located exactly on the vector V extending between the reference clean and dirty pixels 40, 42. An area 44 of three-dimensional space (3D) is defined by the algorithm about the reference clean pixel 40. In particular, the algorithm defines a cylinder 46 about and parallel to the vector V having a base radius r and a height k. The height k is equal to a percentage of the length of the vector V, and represents the degree of cleanliness of the target or test pixel. The end of the cylinder 46 is lined up with the reference clean pixel 40 and a half-sphere 48 is created around the reference clean pixel 40, also having a base radius r.

The algorithm is used to test each pixel of the cleaned area 28 to determine the pixel's location relative to the cylinder 46 and half-sphere 48, for example using traditional distance formulas. The test pixel is evaluated using its k and r values to determine if the target or test pixel lies in the cylinder 46 or half-sphere 48.

Figure 5:
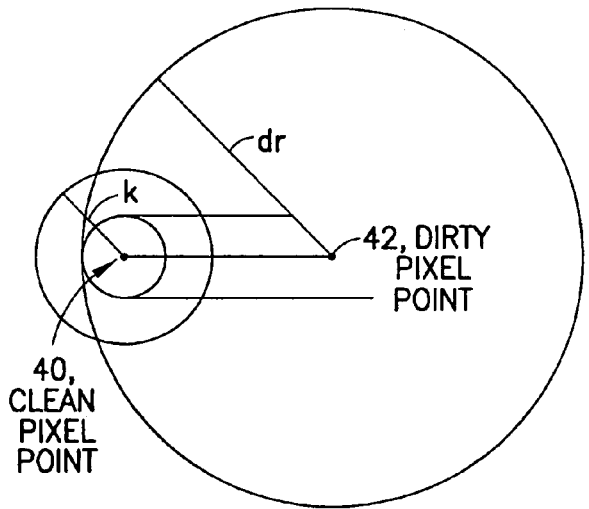
FIG. 5 is a two-dimensional (2D) representation of a portion of the graphical representation of the algorithm illustrated in FIG. 3.

The algorithm may be used to process different "k value" cylinders 46 and half-spheres 44 to determine the amount of target or test pixels contained in ranges of cleanliness such as "60–70%", "70–80%", "80–90%", "90–100%" that may be found in the cleaned area 28. Since the size of the glass panel 14 is known, the total amount of pixels in the glass panel 14 may be used to determine a pixel to square inch or square centimeter conversion. Therefore, the amount of test or target pixels in each clean range in the cleaned area 28 may be determined to a square inch or square centimeter number. The clean ranges (i.e., 60–70%, 70–80%, 80–90% etc.) may then be displayed as a graph, such as a histogram, as shown in FIG. 2. FIG. 5 shows that the algorithm does not need to be adapted to perform three-dimensional (3D) calculations because any three points in space may be connected to create a two-dimensional plane as illustrated in FIG. 5.

EXAMPLE

In the following example, two purge solvent blends are compared to demonstrate each solvent's ability to clean a coating from a coated glass panel. (The two purge solvent blends are identified as Sample A and Sample B in the table below. A glass panel drip test was performed against a redtinted clear coat on the glass panels. The coating was applied at a film thickness of 1.5 mils and tests were conducted using each of Sample A (POLYPURGE 5799) and Sample B (POLYPURGE 6792) both available from PPG Industries, Inc., at 5 and 10 drops.

The glass panels as produced were then scanned digitally into a computer and stored on a hard drive as JPEG images. These images were then processed using a computer program in accordance with the present invention, which employs the algorithm discussed previously. The clean and dirty areas of each glass panel were selected and the dripped area of the glass panel was selected to create the testing boundaries. Each pixel in that area was then processed by determining its RGB value and then comparing that with the 3D vector produced by the RGB values of the reference clean and dirty pixels. Pixels that fell within the target areas defined in 3D space were then counted and converted to square inch values. The results of the testing was as follows:

|  | Sample A 5 Drops | Sample B 5 Drops | Sample A 10 Drops | Sample B 10 Drops |
|---|---|---|---|---|
| Total Image Pixels | 1,972,510 | 1,951,600 | 1,965,568 | 1,945,881 |
| Pixels Processed | 396,408 | 370,944 | 437,241 | 476,890 |
| Total Image Sq Inches | 49 | 49 | 49 | 49 |
| % Clean |  |  |  |  |
| 50 to 59% (Pixels) | 7,313 | 4,462 | 4,897 | 7,387 |
| 60 to 69% (Pixels) | 10,052 | 5,688 | 6,647 | 9,230 |
| 70 to 79% (Pixels) | 16,184 | 11,768 | 10,476 | 11,612 |
| 80 to 89% (Pixels) | 65,730 | 64,249 | 50,163 | 53,043 |
| 90 to 100% (Pixels) | 7,859 | 12,582 | 147,140 | 107,623 |
| 50 to 59% (Sq In) | 0.18 | 0.11 | 0.12 | 0.18 |
| 60 to 69% (Sq In) | 0.25 | 0.14 | 0.17 | 0.23 |
| 70 to 79% (Sq In) | 0.40 | 0.29 | 0.26 | 0.29 |
| 80 to 89% (Sq In) | 1.64 | 1.61 | 1.26 | 1.33 |
| 90 to 100% (Sq In) | 0.20 | 0.31 | 3.69 | 2.69 |
| Sq Inches 50% or Better | 2.68 | 2.47 | 5.51 | 4.73 |
| RGB Values |  |  |  |  |
| Clean Pixel R | 229 | 228 | 231 | 233 |
| Clean Pixel G | 243 | 240 | 245 | 245 |
| Clean Pixel B | 243 | 240 | 246 | 243 |
| Dirty Pixel R | 229 | 235 | 237 | 236 |
| Dirty Pixel G | 175 | 171 | 173 | 170 |
| Dirty Pixel B | 175 | 172 | 173 | 172 |

The glass panels that were produced using 5 drips were nearly identical upon visual inspection, but by using the computer program a slight difference was noted by comparing the areas (in²) that were 50% clean or better. Sample A showed 2.68 total square inches while Sample B showed only 2.47. The superiority of Sample A was not apparent at the 5 drop level but was more evident visually at the 10 drop level. There was a distinct visual difference in the 10 drop test panels and this difference was confirmed using the computer program which showed a 5.51 square inch value for Sample A versus the 4.73 square inch value for Sample B. The results for Sample B are provided in histogram form in FIG. 2.

While the present invention was described with reference to preferred embodiments of a method and apparatus for evaluating quantitatively the ability of a solvent to clean a coating from a substrate using a glass panel drip test, those skilled in the art may make modifications and alterations to the present invention without departing from the scope and spirit of the invention. Accordingly, the above-detailed description is intended to be illustrative rather than restrictive. The invention is defined by the appended claims, and all changes to the invention that fall within the meaning and range of equivalency of the claims are to be embraced within their scope.

I claim:

1. A method of evaluating quantitatively the ability of a solvent to clean a coating from a substrate using a glass panel drip test, comprising:
   conducting a drip test on a coated glass panel;
   placing a template behind the glass panel;
   digitally acquiring an image of the glass panel and template into a computer;
   evaluating the glass panel for cleanliness based on the digital image of the glass panel and template; and
   processing the digital image of the glass panel and template to determine actual area of the glass panel cleaned by the drop test greater than a pre-specified value.

2. The method of claim 1, wherein the pre-specified value is a pre-specified percentage.

3. A method of evaluating quantitatively the ability of a solvent to clean a coating from a substrate using a glass panel drip tests, comprising:
   conducting a drip test on a coated glass panel;
   placing a template behind the glass panel;
   optically scanning the glass panel and template into a computer to form a digital image of the glass panel surface; and
   processing the digital image of the glass panel surface to determine cleanliness of the area of the glass panel surface subjected to the drip test comprising determining actual area of the glass panel surface subjected to the drip test greater than a pre-specified value.

4. The method of claim 3, wherein the pre-specified value is a pre-specified percentage.

5. A method of evaluating quantitatively the ability of a solvent to clean a coating from a substrate using a glass panel drip tests, comprising:
   conducting a drip test on a coated glass panel;
   placing a template behind the glass panel;
   optically scanning the glass panel and template into a computer to form a digital image of the glass panel surface wherein the digital image comprises pixels;
   processing the digital image of the glass Panel surface to determine cleanliness of the area of the glass panel surface subjected to the drip test; and
   evaluating the pixels of the digital image using a computer algorithm to determine how many pixels from the area of the glass panel surface subjected to the drip test have been cleaned.

6. The method of claim 5, wherein the step of evaluating the pixels comprises using image analysis of the pixels to quantify the actual area of the glass panel cleaned by the drip test greater than a pre-specified percentage.

7. The method of claim 5, wherein the step of evaluating the pixels comprises identifying a reference clean pixel from an uncoated area of the glass panel surface, identifying a reference dirty pixel from a coated area of the glass panel surface not subjected to the drip test, and comparing individually the pixels from the area of the glass panel surface subjected to the drip test with the reference clean and dirty pixels.

8. The method of claim 7, wherein the step of comparing individually the pixels from the area of the glass panel surface subjected to the drip test with the reference clean and dirty pixels further comprises calculating percent of cleanliness of each of the pixels from the area of the glass panel subjected to the drip test relative to the reference clean and dirty pixels.

9. The method of claim 8, further comprising displaying the percent of cleanliness values of each of the pixels from the area of the glass panel subjected to the drip test as a graph.

10. The method of claim 5, wherein the step of evaluating the pixels comprises using image analysis of the pixels to quantify the actual area of the glass panel cleaned by the drop test greater than a pre-specified value.

11. The method of claim 10, wherein the pre-specified value is a pre-specified percentage.

12. The method of claim 5, further comprising assigning color values to the pixels of the digital image and evaluating the color values using a computer algorithm to determine how many pixels from the area of the glass panel surface subjected to the drip test have been cleaned.

13. The method of claim 12, wherein the step of evaluating the color values comprises identifying the color value of a reference clean pixel from an uncoated area of the glass panel surface, identifying the color value of a reference dirty pixel from a coated area of the glass panel surface not subjected to the drip test, and comparing individually the color values of the pixels from the area of the glass panel surface subjected to the drip test with the color values of the reference clean and dirty pixels.

14. The method of claim 13, wherein the step of comparing individually the color values of the pixels from the area of the glass panel surface subjected to the drip test with the color values of the reference clean and dirty pixels further comprises calculating percent of cleanliness using the color values of the pixels from the area of the glass panel subjected to the drip test relative to the color values of the reference clean and dirty pixels.

15. The method of claim 13, further comprising displaying the percent of cleanliness values of each of the pixels from the area of the glass panel subjected to the drip test as a graph.

* * * * *